United States Patent
Moimas et al.

(10) Patent No.: US 8,093,166 B2
(45) Date of Patent: Jan. 10, 2012

(54) BIOACTIVE GLASS COMPOSITIONS

(75) Inventors: Loredana Moimas, Ylöjärvi (FI); Eija Pirhonen, Tampere (FI)

(73) Assignee: Inion Oy, Tampere (FI)

(*) Notice: Subject to any disclaimer, the term of this patent is extended or adjusted under 35 U.S.C. 154(b) by 944 days.

(21) Appl. No.: 11/743,769

(22) Filed: May 3, 2007

(65) Prior Publication Data

US 2008/0066495 A1    Mar. 20, 2008

(30) Foreign Application Priority Data

Sep. 20, 2006 (EP) .................................. 06120965

(51) Int. Cl.
  *C03C 3/097* (2006.01)
  *C03C 3/089* (2006.01)
  *C03C 3/078* (2006.01)
(52) U.S. Cl. ............................... 501/63; 501/65; 501/72
(58) Field of Classification Search .................... 501/63, 501/65, 72
See application file for complete search history.

(56) References Cited

U.S. PATENT DOCUMENTS

2005/0201987 A1 * 9/2005 Pirhonen et al. ............. 424/93.7

FOREIGN PATENT DOCUMENTS

| EP | 1 405 647 | 4/2004 |
|---|---|---|
| EP | 1 449 815 | 8/2004 |
| EP | 1 655 042 | 5/2006 |
| WO | WO 91/12032 | 8/1991 |
| WO | WO 91/17777 | 11/1991 |
| WO | WO 96/21628 | 7/1996 |
| WO | WO 03/050052 A1 * | 6/2003 |
| WO | WO 2005/084727 | 9/2005 |

OTHER PUBLICATIONS

English abstract of EP 1 449 815.

* cited by examiner

*Primary Examiner* — David M. Brunsman
*Assistant Examiner* — Kevin Johnson
(74) *Attorney, Agent, or Firm* — Banner & Witcoff, Ltd.

(57) ABSTRACT

A bioactive glass composition, a method and an implant. The glass composition comprising $SiO_2$, $Na_2O$, $K_2O$, CaO, and $P_2O_5$, having the following composition: $SiO_2$ 48-52 wt-%, $Na_2O$ 9-15 wt-%, $K_2O$ 12-18 wt-%, CaO 10-16 wt-%, $P_2O_5$ 1-7 wt-%, $TiO_2$ 0.2-2 wt-%, $B_2O_3$ 0-4 wt-%, and MgO 0-6 wt-%, wherein $Na_2O+K_2O>25$ wt-%, $MgO+CaO>14$ wt-%, and $B_2O_3/P_2O_5>0.3$.

14 Claims, 1 Drawing Sheet

# BIOACTIVE GLASS COMPOSITIONS

RELATED APPLICATION

This application claims the benefit of the filing date of European application no. 06120965.6, filed Sep. 20, 2006, which is hereby incorporated herein by reference in its entirety for all purposes.

FIELD OF THE INVENTION

The present invention relates to a bioactive glass composition comprising $SiO_2$, $Na_2O$, $K_2O$, CaO, and $P_2O_5$.

BACKGROUND OF THE INVENTION

In this description, a bioactive material refers to a material designed to induce specific biological activity in a body tissue. Bioactive glass refers to any glass that displays characteristics of bioactivity. Bioactive glass is an amorphous solid that is not intrinsically adhesive and that is capable of forming a cohesive bond with both hard and soft tissue when exposed to appropriate in vivo and in vitro environments, such as simulated body fluid or tris-hydroxymethylaminomethane buffers. A cohesive bond is achieved by developing a surface layer of hydroxycarbonate apatite onto the bioactive glass through the release of ionic species from the bulk bioglass material.

Numerous applications have been found for bioactive glasses in the field of surgical and orthopedic treatments as well as in dental surgery.

A variety of bioactive glass compositions has been presented in the literature and patents. Bioactive glass compositions have been described, for instance, in European Patent 1 405 647 and European Patent Application 1 655 042, as well as in International applications WO 96/21628, WO 91/17777, and WO 91/12032.

However, the known bioactive glass compositions have a common disadvantage in that they are inherently difficult to control while being processed into products, especially when being processed into fibers in a melt-spinning process. Such troubled controllability means, for example, that the diameters of the fibers fluctuate considerably, crystallites forms into glass which leads to inhomogenity of fibers or devitrification of glass, which lowers the yield of a fiber manufacturing process. The fluctuation in fiber diameter and inhomogenity of fibers have a negative influence on further processes where the equipment and processing parameters should be fixed at least partly based on the diameter of the processed fibers. Such processes and parameters include a sintering temperature in sintering processes. Fluctuation in fiber diameter also affects e.g. the quality of the final product because thinner fibers behave in a different manner than thicker fibers. The manufacture of spherical particles and coatings is also affected by the fluctuating or non-homogenous behavior in their manufacturing processes.

In addition to the physical dimensions of the fibers or other products also some chemical features are difficult to control. For example, variation in local oxides concentration may occur, which also affects the degradation profile of the material and the ionic release profile.

Furthermore, some manufacturing related processes, for example crucible cleaning and fiber sieving, are difficult and time-consuming to be carried out.

Another drawback of the known bioactive glass compositions is that their yield in melt-spinning process is fairly low.

BRIEF DESCRIPTION OF THE INVENTION

An object of the present invention is to provide novel bioactive glass compositions to alleviate the above disadvantages.

The bioactive glass compositions of the invention are characterized by the following composition:

| | |
|---|---|
| $SiO_2$ | 48-52 wt-%, |
| $Na_2O$ | 9-15 wt-%, |
| $K_2O$ | 12-18 wt-%, |
| CaO | 12-18 wt-%, |
| $P_2O_5$ | 0-4 wt-%, |
| $TiO_2$ | 0-2 wt-%, |
| $B_2O_3$ | 1-4 wt-%, and |
| MgO | 0-5 wt-%, wherein |
| $Na_2O + K_2O$ | >25 wt-%, |
| MgO + CaO | >14 wt-%, and |
| $B_2O_3/P_2O_5$ | >0.3. |

$B_2O_3$ and $P_2O_5$ are known to be glass network formers as $SiO_2$. $P_2O_5$ has an adverse effect with respect to a working temperature range of the glass material as it increases crystallization, but has a positive effect on the bioactivity of the resulting bioactive glass. $B_2O_3$ has been shown to increase osteointegration properties of the final bioactive glass material, and it was found that it could be used to compensate for the negative effect of $P_2O_5$ on manufacturing processes. In particular, it was found that by choosing the aforesaid ratio of $B_2O_3/P_2O_5$, the beneficial effects of both oxides on the properties of the material are maximized.

The invention is based on the surprising fact found out by the inventors that glasses with the claimed composition range possess surprisingly good performance in manufacturing processes when compared to glasses out of this range.

An advantage of the invention is that a more controllable manufacturing process is achieved, especially in manufacturing of bioactive glass fibers. This means that the glass is easier to manufacture and, in particular, the homogeneity of the glass is higher, meaning, for instance, a higher fiber manufacturing yield and better fiber properties. Another advantage of the present invention is that the glass can be repeatedly heat-treated without the glass crystallizing or changing its surface or bulk properties. A further advantage of the present invention is that the yield is improved when fibers are manufactured. It was also observed that a crucible is easier to clean when glasses having this specified compositional range have been used.

BRIEF DESCRIPTION OF THE DRAWINGS

In the following, the invention will be described in greater detail with reference to the attached drawings, in which.

DETAILED DESCRIPTION OF THE INVENTION

Figure 1:
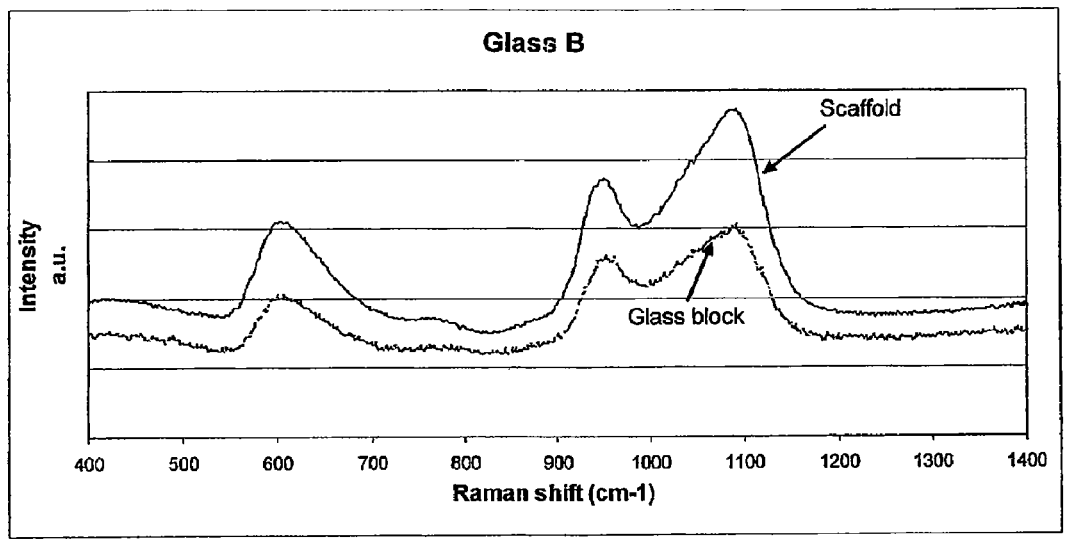
FIG. 1 represents Raman spectra of a bioactive glass composition according to the invention.
Figure 2:
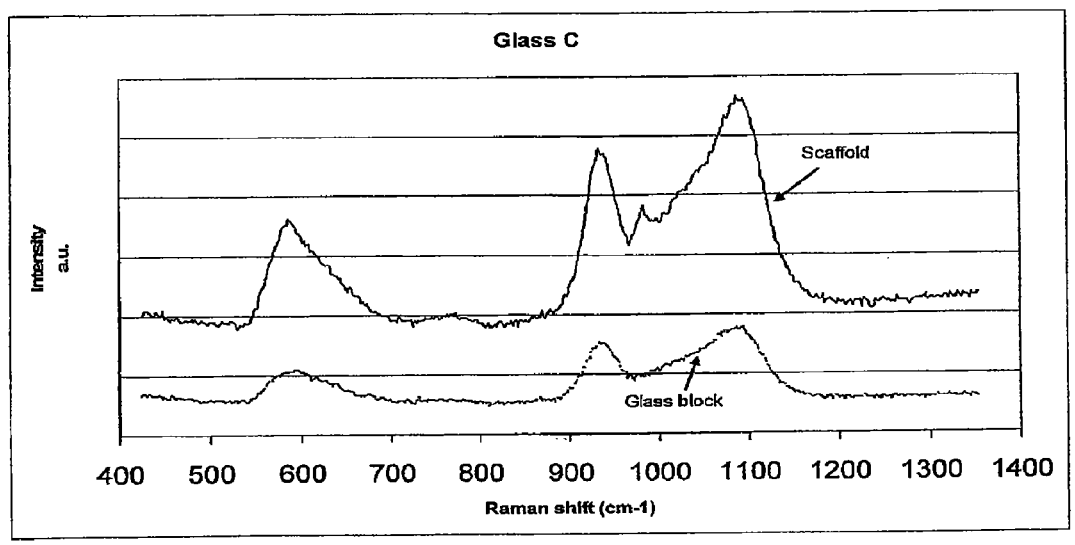
FIG. 2 represents Raman spectra of a prior art bioactive glass composition.

Bioactive glass compositions of the invention have the following composition range:

| | |
|---|---|
| SiO₂ | 48-52 wt-%, |
| Na₂O | 9-15 wt-%, |
| K₂O | 12-18 wt-%, |
| CaO | 12-18 wt-%, |
| P₂O₅ | 0-4 wt-%, |
| TiO₂ | 0-2 wt-%, |
| B₂O₃ | 1-4 wt-%, and |
| MgO | 0-5 wt-%, wherein |
| Na₂O + K₂O | >25 wt-%, |
| MgO + CaO | >14 wt-%, and |
| B₂O₃/P₂O₅ | >0.3. |

It should be noted that below bioactive glass is referred to as "glass."

Example 1

Fifteen batches of bioactive glasses with five different compositions were manufactured (three batches with each composition). The compositions are given as calculated theoretical starting compositions. Raw materials used for the manufactured bioactive glasses were analytical grade $Na_2CO_3$, $K_2CO_3$, $MgO$, $TiO_2$, $B_2O_3$, $CaCO_3$, $CaHPO_4 \cdot 2H_2O$ as well as $SiO_2$. The raw materials were weighed and mixed in a plastic container and then melted in a platinum crucible for three hours at 1360° C. In order to achieve homogeneous glass, the formed glass was then crushed into pieces of approximately 1 cm³ and re-heated for 3 hours at 1360° C. With this method, solid glass blocks with masses of approximately 230 g were achieved. The same manufacturing method was used to manufacture all five types of bioactive glasses, A, B, C, D and E. Table 1 shows the compositions of the formed bioactive glasses.

Any other known processes or equipment can be used to manufacture compositions of the invention. The thermal cycles of the processes can be optimized for each glass. It is to be noted that it is not necessary to crush and reheat the glass. It is also possible to use raw materials other than those disclosed above. For example, CaO can be used instead of $CaCO_3$.

TABLE 1

Compositions of formed glasses as weight-%.

| | Wt % | | | | | | | |
|---|---|---|---|---|---|---|---|---|
| | Na₂O | K₂O | MgO | CaO | B₂O₃ | P₂O₅ | TiO₂ | SiO₂ |
| glass A | 6.0 | 12.0 | 5.0 | 20.0 | 0 | 4.0 | 0 | 53.0 |
| glass B | 11.7 | 16.3 | 3.1 | 13.0 | 1.4 | 3.3 | 0.6 | 50.6 |
| glass C | 18.0 | 9.0 | 0 | 14.0 | 1.0 | 4.0 | 0 | 54.0 |
| glass D | 8.8 | 11.0 | 4.0 | 22.7 | 1.0 | 1.5 | 0 | 51.0 |
| glass E | 11.6 | 14.7 | 3.1 | 12.8 | 1.4 | 6.4 | 0 | 50 |

Glass B has a composition according to the invention, whereas glasses A, C, D and E are outside the ranges of the composition of the invention. All glass batches from compositions A, B, C and D formed a clear, transparent glass block with no signs of crystallinity in it. In the glass blocks manufactured with recipe E, crystallites could be seen in the formed glass block, and glass E was discarded from further processes and analysis.

Fibers were manufactured from each manufactured glass blocks as follows. The glass block was first placed into a platinum crucible, which had 7 orifices with a diameter of 3.8 mm at the bottom of the crucible. The crucible was then placed into the furnace (LINDBERG/BLUE CF56622C, by LINDBERG/BLUE, N.C., U.S.A), which had an opening at the bottom. For each fiber composition an optimal temperature for fiber spinning had been found out prior this experiment by performing fiber spinning trials using different temperatures. On the basis of these pilot trials, the optimal fiber spinning temperatures were found as follows: 930° C. for glass A, 810° C. for glass B, 820° C. for glass C and 900° C. for glass D.

The lower the optimal temperature the better it is for the manufacturing of the fibers because the fibers then come to contact with rolls at a lower temperature, thus decreasing the possibility of the coating material of the rolls being damaged and of the fibers being stacked onto the coating such that they begin to move around the rolls, in which case an operator cannot collect them.

At the optimal temperature, the glass melted and started to run from the orifices and the formed fibers were then drawn with a spinning roll. By controlling the speed of the roll, it was possible to control the diameter of the fibers. The speed of the spinning rolls was adjusted such that a fiber diameter of 0.75 mm was obtained.

The fiber spinning was carried out as long as fibers were successfully drawn. Glass fibers obtained were further chopped into a length of 3±2 mm within the fiber spinning process using a cutter.

After the fibers were manufactured, the yield of the process was measured from each manufactured batch. This was carried out by weighing the mass of fibers obtained and dividing the mass by the mass of glass block initially used. The yield of the glasses is shown in Table 2.

TABLE 2

Yield of spinning processes.

| Yield | Glass A | Glass B | Glass C | Glass D |
|---|---|---|---|---|
| % | 51 ± 5 | 82 ± 3 | 48 ± 5 | 43 ± 7 |

It is clear that glass B, i.e. the glass composition according to the invention, has a notably improved yield when compared to the other glass compositions.

The manufactured glass fibers were further evaluated under a light microscope (Smartscope flash, Optical Gauging Products Inc.) in order to analyze the fiber diameter distribution of the fibers. From each batch of glass fibers, the diameters of 200 randomly selected fibers were measured. On the basis of the measurements, fiber diameter distribution curves for each glass compositions were achieved. Table 3 shows results of the analysis for each four glass compositions.

TABLE 3

Results of fiber diameter distribution analysis.

| | Fiber diam. | | |
|---|---|---|---|
| | 73-77 μm | 70-80 μm | 65-85 μm |
| glass A | 68% | 84% | 96% |
| glass B | 82% | 92% | 98% |
| glass C | 59% | 79% | 95% |
| glass D | 56% | 78% | 93% |

As can be seen in Table 3, about 80% of the fibers of the glass composition of the invention, i.e. glass B, has a diameter in the range of 73 to 77 μm. Meanwhile, the fibers of glasses A, C and D have distributions where about 80% of the fiber diameters is spread within a much wider range of 70 to 80 μm. This is a significant discrepancy in the fiber diameter distribution, meaning that the controllability of the fiber manufacturing process is much better when glass compositions of the invention are used instead of known glass compositions.

Example 2

Glass fibers were first manufactured from glasses A and B as described in Examples 1 and 2. In order to form a solid porous scaffold from the manufactured glass fibers, various sintering methods can be used. In order to find the optimal sintering temperature for each glass composition, the following study was performed. Approximately 2 grams of the chopped fibers from a glass composition were randomly placed as a huddle on a ceramic plate. Then the plate, together with the huddle, was placed into a heated furnace to be heated for 45 minutes.

The furnace temperature was varied in order to find the optimal temperature range for each glass composition. In the optimum temperature range, the glass fibers slightly sintered together and formed a porous scaffold. A scaffold is a porous structural device that allows living tissues to grow into it. A scaffold can form, for instance, a base that serves as a guide for tissue growth. The scaffold has a certain porosity. The porosity refers to the volume percentage of air in the three-dimensional scaffold. If the temperature was too low, the fibers remained individual and did not sinter together. When the temperature was too high, the fibers melted completely and lost their fibrous form, and a drop of solid glass was formed. Ideally, the chopped glass fibers form a porous network or scaffold in which individual glass fibers retain their fibrous form but form a solid joint at points where individual fibers come into contact with each other. Table 4 shows the ideal temperature range for the glasses.

TABLE 4

Sintering temperature range for glasses A and B.

| | Sintering temp. | |
| --- | --- | --- |
| | Lower limit | Upper limit |
| Glass A | 690° C. | 740° C. |
| Glass B | 590° C. | 620° C. |

As can be seen in Table 4, the temperature range for glass B is the lowest one. This means lower sintering temperatures and, therefore, lower energy consumption in heating. A heating time of 45 minutes can be a preferable time for sintering when using ceramic plates or molds. Instead, if titanium plates or molds are used the time can be reduced to less than 20 minutes. This is due to the better thermal conductivity of titanium.

Sintering temperatures of the present invention for glass fibers may vary from about 500° C. to about 700° C., preferably from about 550° C. to about 650° C., and most preferably from about 590° C. to about 620° C.

It is to be noted that chopped fibers preferably have a length of about 0.5 mm to about 10 mm, and more preferably the length of the fibers is approximately about 1 mm to about 5 mm. Controlling the length of the fibers is a way to adjust the size of the pores of the sintered scaffold to a desired level.

Porous sintered forms of glasses can be used, for instance, as bone fillers or soft tissue fillers. It is also possible to sinter crushed or spherical granules or some other form of glass into the form of a porous scaffold.

The fibers usually have a diameter of about 0.010 to about 1.0 mm, and preferably have a diameter of about 0.030 to about 0.300 mm. By altering the diameter of the fibers, the rate of dissolution can be controlled. Lower sintering temperatures may be used for fibers with smaller diameter, and the porosity of the scaffold can be tailored. By altering the processing parameters, the properties of the scaffold can be adjusted to a desired level and, for example, a scaffold which is easily formable for example with a knife can be prepared.

Example 3

Glass scaffolds were manufactured from glass compositions B and C as described in Examples 1 and 2. The scaffolds manufactured from glass B were sintered at 610° C. for 45 minutes and the scaffolds manufactured from glass C at 620° C. for 45 minutes. The obtained scaffolds were further analyzed with Raman spectroscopy (Renishaw) in order to analyze crystalline formation in the glasses.

As can be seen in Raman spectroscopy graphs shown in FIGS. 1 (glass B) and 2 (glass C), glass B remains amorphous over the fiber spinning and sintering processes. In the scaffolds manufactured from glass C, the glass is initially amorphous after glass formation but after fiber manufacture and sintering steps, clear peaks indicating crystalline phases in the structure can be observed.

In other words, glass B can be repeatedly heat-treated without the glass crystallizing. It is also discovered that glass compositions of the invention do not change their surface or bulk properties in repeated heatings.

By sintering glass fibers, a porous osteoconductive scaffold can be formed. Osteoconduction is a process of passively allowing bone to grow and remodel over a surface. In osteoconduction, an implant provides a biocompatible interface along which bone migrates.

By optimizing the processing parameters the degree of porosity can be controlled. The porosity of the scaffold can be within the range of about 5 to about 95 volume-%, and preferably about 20 to about 80 volume-%.

In another embodiment of the present invention, sintering of the glass fibers is performed under load, which means that the fibers are pressed, more or less, together during the sintering. Sintering under load usually results in a more homogenous structure of the scaffold. A compression load can be, for instance, within the range of about 10 kPa to 1000 kPa, at least.

The preferred sintering time in this invention is about 1 to about 120 minutes, and preferably about 5 to about 30 minutes.

Example 4

Sixteen batches F to U of glasses of the invention with different compositions were manufactured, and fibers were manufactured from the glasses as described in Example 1. The yield of the fiber manufacturing process was measured for each glass. The calculated theoretical compositions of the glasses and the yield in the fiber manufacturing process are shown in Table 5.

TABLE 5

Compositions of manufactured glasses as weight-% and yield of fiber manufacturing process.

| | Na$_2$O | K$_2$O | MgO | CaO | B$_2$O$_3$ | P$_2$O$_5$ | TiO$_2$ | SiO$_2$ | Yield (%) |
| --- | --- | --- | --- | --- | --- | --- | --- | --- | --- |
| F | 11.8 | 16.3 | 3.1 | 13.0 | 1.4 | 3.3 | 0.5 | 50.6 | 77 |
| G | 11.8 | 16.5 | 3.1 | 12.7 | 1.3 | 3.3 | 0.5 | 50.8 | 76 |
| H | 11.7 | 16.2 | 3.1 | 13.2 | 1.3 | 3.1 | 0.4 | 51.0 | 77 |

TABLE 5-continued

Compositions of manufactured glasses as weight-% and yield of fiber manufacturing process.

| | $Na_2O$ | $K_2O$ | MgO | CaO | $B_2O_3$ | $P_2O_5$ | $TiO_2$ | $SiO_2$ | Yield (%) |
|---|---|---|---|---|---|---|---|---|---|
| I | 11.1 | 16.2 | 3.1 | 13.8 | 1.3 | 3.1 | 0.4 | 51.0 | 80 |
| J | 11.1 | 16.2 | 3.1 | 13.8 | 1.2 | 3.1 | 0.4 | 51.1 | 78 |
| K | 11.2 | 16.2 | 3.1 | 13.9 | 1.0 | 3.1 | 0.4 | 51.1 | 75 |
| L | 11.2 | 16.2 | 3.1 | 14.0 | 1.0 | 3.1 | 0.4 | 51.0 | 75 |
| M | 11.4 | 16.3 | 2.8 | 14.3 | 1.0 | 2.8 | 0.4 | 51.0 | 77 |
| N | 11.4 | 16.7 | 3.1 | 13.5 | 1.4 | 3.8 | 0.0 | 50.1 | 76 |
| O | 11.3 | 17.1 | 3.2 | 15.2 | 1.4 | 3.3 | 0.0 | 48.5 | 70 |
| P | 11.8 | 15.0 | 3.2 | 13.0 | 1.4 | 3.6 | 0.0 | 52.0 | 75 |
| Q | 12.0 | 15.3 | 3.3 | 13.3 | 1.3 | 3.3 | 0.0 | 51.5 | 82 |
| R | 11.7 | 17.0 | 3.2 | 13.0 | 1.4 | 2.7 | 0.0 | 51.0 | 79 |
| S | 11.2 | 16.2 | 3.1 | 13.9 | 1.1 | 3.1 | 0.4 | 51.0 | 77 |
| T | 11.2 | 16.2 | 3.1 | 14.0 | 1.0 | 3.1 | 0.4 | 51.0 | 75 |
| U | 11.5 | 16.2 | 2.8 | 14.2 | 1.0 | 2.9 | 0.4 | 51.0 | 78 |

As can be seen in Table 5, the glass compositions according to the invention have a high yield as compared, for instance, with the known glass compositions A, C and D in Table 2.

Example 5

In order to analyze the variation between the theoretical calculated compositions and the composition of the glasses after the glass manufacturing process, three different glass fiber batches with different compositions were manufactured. Elemental analyzes were performed on each manufactured glass block. The elemental analyzes were carried out with X-ray spectroscopy (Philips PW 2404 RGT). Table 6 shows the theoretical calculated values and data from the compositional analysis for glasses V, X and Y. Only minor changes in compositions exist between the theoretical and analyzed values.

TABLE 6

Theoretical calculated values and compositional analysis data for glasses V, X and Y.

| Glass | $Na_2O$ | $K_2O$ | MgO | CaO | $B_2O_3$ | $P_2O_5$ | $TiO_2$ | $SiO_2$ |
|---|---|---|---|---|---|---|---|---|
| V (theoretical) | 11.74 | 16.37 | 3.155 | 12.99 | 1.417 | 3.333 | 0.592 | 50.7 |
| V (analysis data) | 11.5 | 15.4 | 3.24 | 12.5 | * | 3.29 | 0.312 | 50.9 |
| X (theoretical) | 11.81 | 15.88 | 3.17 | 13.07 | 1.21 | 2.68 | 0.2 | 51.97 |
| X (analysis data) | 11.5 | 15.1 | 3.25 | 12.5 | * | 2.62 | 0.216 | 52.2 |
| Y (theoretical) | 11.73 | 16.51 | 3.153 | 12.72 | 1.307 | 3.331 | 0.588 | 50.95 |
| Y (analysis data) | 11.4 | 15.6 | 3.22 | 12.1 | * | 3.28 | 0.315 | 51.0 |

* Element not detectable with this method

Example 6

Bioactive glass fibers with a nominal diameter of 75 μm were first manufactured from glass B, as described in Example 1. The manufactured fibers were further chopped manually using scissors to a nominal length of 5 mm. P(L/DL)LA 70/30 polymer was then solved into acetone and the chopped fibers were admixed to the viscous solution to form composite preforms containing glass fibers and P(L/DL)LA 70/30 polymer. To allow the acetone to evaporate, the solution was then spread into a flat container for approximately 24 hours. The sheet-like composite preforms were then cut into square billets of approximately 1 cm×1 cm. The composite billets were next dried in a vacuum oven at room temperature for 3 days and then at 80° C. for 16 hours to ensure that all the acetone had evaporated.

Five different compositions were produced as described above, containing 0, 10, 20, 30, and 40 volume-% of glass fibers. A piston injection molder (SP2 Chippenham, England) with a steel mold was used to form composite rods from the billets. Rods were successfully manufactured from each of the five different composite compositions.

Glass fibers can also be used as reinforcing elements in a polymer matrix of an implant. Reinforced composite implants can be used as fixation plates, etc.

Example 7

Bioactive glass compositions F, G, H and I were manufactured and their properties at a high temperature were analyzed using a hot stage microscope. The analysis allows determination of the characteristic temperatures of sintering, softening, sphere, half-sphere and melting.

TABLE 7

Sintering, softening, sphere, half sphere and melting temperatures for glass compositions F, G, H, I, J.

| Glass | Sintering | Softening | Sphere | Half sphere | Melting |
|---|---|---|---|---|---|
| F | 599 | 647 | 790 | 910 | 934 |
| G | 598 | 691 | 777 | 900 | 929 |
| H | 600 | 642 | 754 | 913 | 938 |
| I | 609 | 689 | 805 | 917 | 941 |
| J | 615 | 638 | 795 | 923 | 944 |

As can be seen in Table 7, the sintering temperatures of all the analyzed glass compositions reside within a range of 590 to 620° C. In addition, for all the compositions, the characteristic temperatures are all similar, meaning that the materials are all characterized by similar high temperatures and, in particular, high-temperature manufacture properties.

In an embodiment of the present invention a porous scaffold manufactured by sintering glass fibers can be attached to a biocompatible polymeric film such that the scaffold has a barrier property on at least one of its side. This kind of composite structure can be used for example with guided bone regeneration where a barrier effect is required to avoid soft tissue ingrowth in the area where new bone formation is required. Another application of the composite structure is in regeneration of cartilage tissue. The porous scaffold sintered from glass fibers is able to form a matrix into which cartilage tissue can grow. The other side of the scaffold with polymeric film serves as a barrier that separates the newly formed cartilage tissue from the synovial liquids.

The biocompatible film can be prepared, for instance, of polyglycolide, polylactide, poly-β-hydroxybutyric acid, polydioxanone, polyvinylalcohol, polyesteramine, their copolymers or polymer blends thereof. Any other resorbable or nonresorbable biocompatible polymer can also be used for the preparation of the biocompatible film.

In still another embodiment of the present application, the glass fibers are first coated with a biocompatible polymer phase prior to sintering. The fibers are chopped, and then the coated fibers are sintered to form a three-dimensional scaffold. In such a case, the scaffold has a reasonably elastic performance, and can be applied to cases where elastic performance is required from the scaffold. Suitable biocompatible polymers include polyglycolide, polylactide, polyhydroxybutyric acid, polydioxanone, polyvinylalcohol, polyesteramine, their copolymers and polymer blends thereof. The sintering time of the present invention for sintering glass fibers coated with polymers is about 1 to about 120 minutes, and preferably about 5 to about 30 minutes.

When fibers coated with biocompatible polymers are sintered, the sintering temperature depends on the softening point of the coat polymer. When biocompatible polymers are used the sintering temperature is about 50° C. to about 300° C., and preferably about 100° C. to about 200° C.

The thickness of the polymer coating on the fibers is from about 1 to about 200 µm, preferably from about 5 to about 30 µm.

In another embodiment of the present invention, bioactive agents can be used in combination with devices made of the composition of the invention to promote new tissue, e.g. bone, formation. In such a case, the porous scaffold made from the glass can act as a carrier for bioactive agents. The biologically active agent can be selected from the group consisting of anti-inflammatory agents, antibacterial agents, antiparasitic agents, antifungal agents, antiviral agents, anti-neoplastic agents, analgesic agents, anaesthetics, vaccines, central nervous system agents, growth factors, hormones, antihistamines, osteoinductive agents, cardiovascular agents, anti-ulcer agents, bronchodilators, vasodilators, birth control agents, fertility enhancing agents, and polypeptides. Preferably, the bioactive agents are bone morphogenic proteins (BMP), such as OP-1, BMP-2, BMP-4 and BMP-7, or pyrrolidones. The pyrrolidones useful in the present invention include any pyrrolidone known in the art of chemistry to have a plasticizing or solubilizing properties without having tissue impairing effects or toxic effects. Such pyrrolidones include, alkyl- or cycloalkyl-substituted pyrrolidones, such as 1-methyl-2-pyrrolidone (NMP), 1-ethyl-2-pyrrolidone (NEP), 2-pyrrolidone (PB), and 1-cyclohexyl-2-pyrrolidone (CP), NMP and NEP being preferred examples. Additionally, pyrrolidone-based polymers, such as polyvinylpyrrolidones, may also be useful in the material of the invention. The pyrrolidone can be arranged in the composition by using methods disclosed, for instance, in Example 1 of WO2005/084727, which is hereby incorporated by reference herein.

The glasses of the invention have a large working range with improved forming properties. The glasses can therefore be formed with different methods, e.g. by flame spraying to form, for instance, spherical particles. The spherical particles can be used e.g. as a target in radiotherapy in cancer treatment e.g. for internal radionuclide therapy of liver tumors. The spherical particles can also be used as an abrasive of diseased and infected tissues, and in dentistry for cleaning and smoothing of a tooth surface.

The glasses of the invention can also be utilized in the manufacture of composite products e.g. by compression molding or other methods known per se.

The glasses can be formed by various blowing methods known in the field of technical grade glasses for the manufacture of even more complicated shapes. Furthermore, the glasses can be processed by fiber spinning to form fibers.

The glasses of the invention can also be cast, for example into three-dimensional products. Cast solid forms of glass can be used e.g. as supporting plates in surgery e.g. for the treatment of a broken orbital floor.

There are also other applications not mentioned above where glasses of the invention can be used. For example, they can be used as a coating of biostable implants to improve tissue attachment of an implant.

Glass fibers are potential material to be applied to tissue engineering to regenerate nerves. The bioactive glass fiber behaves as a temporary scaffold for neurons, since neurons can grow and form long fibrous structures when they are grown in close contact with glass fiber.

Glass fibers can possibly be applied to tissue engineering to regenerate myocardial cells, and other muscular cells.

In addition, glass compositions of the invention have some angiogenetic properties, i.e. they activate the growth of blood vessels. Therefore, the glass could be used for tissue engineering of vascularized tissues in general.

It will be obvious to a person skilled in the art that as technology advances, the inventive concept can be implemented in various ways. The invention and its embodiments are not limited to the examples described above or below but may vary within the scope of the claims.

What is claimed is:

1. A bioactive glass composition comprising 48.5-52.0 wt-% of $SiO_2$, 11.1-12.0 wt % of $Na_2O$, 15.0-17.1 wt-% of $K_2O$, 12.7-15.2 wt-% of CaO, 2.7-3.8 wt-% of $P_2O_5$, 0.0-0.6 wt-% of $TiO_2$, 1.0-1.4 wt-% of $B_2O_3$, and 2.8-3.3 wt-% of MgO;
   wherein the bioactive glass composition is amorphous.

2. A bioactive glass composition according to claim 1, comprising 51.0 wt-% of $SiO_2$, 11.1 wt-% of $Na_2O$, 16.2 wt-% of $K_2O$, 13.8 wt-% of CaO, 3.1 wt-% of $P_2O_5$, 0.4 wt-% of $TiO_2$, 1.3 wt-% of $B_2O_3$, and 3.1 wt-% of MgO.

3. A bioactive glass composition according to claim 1, comprising 51.1 wt-% of $SiO_2$, 11.1 wt-% of $Na_2O$, 16.2 wt-% of $K_2O$, 13.8 wt-% of CaO, 3.1 wt-% of $P_2O_5$, 0.4 wt-% of $TiO_2$, 1.2 wt-% of $B_2O_3$, and 3.1 wt-% of MgO.

4. A bioactive glass composition according to claim 1, comprising 50.6 wt-% of $SiO_2$, 11.8 wt-% of $Na_2O$, 16.3 wt-% of $K_2O$, 13.0 wt-% of CaO, 3.3 wt-% of $P_2O_5$, 0.5 wt-% of $TiO_2$, 1.4 wt-% of $B_2O_3$, and 3.1 wt-% of MgO.

5. A method for performing surgery, comprising the step of implanting a sintered scaffold comprising a bioactive glass composition according to claim 1.

6. A method for manufacturing a bioactive glass composition, comprising the steps of:
   selecting raw materials for the composition,
   mixing the raw materials, and
   melting the raw materials into a homogenous glass;
   wherein the raw materials are selected such that the homogenous glass has a composition according to claim 1.

7. An implant comprising a bioactive glass composition according to claim 1.

8. An implant according to claim 7, wherein the implant has at least a partly porous structure made of the bioactive glass composition.

9. An implant according to claim 8, wherein the porous structure comprises sintered fibers.

10. An implant according to claim 7, wherein the implant further comprises a polymer phase.

11. An implant according to claim 10, wherein the implant comprises the bioactive glass composition coated at least partly with a polymer coating.

12. An implant according to claim 10, wherein the implant comprises bioactive glass fibers embedded in a polymer matrix.

13. An implant according to claim 10, wherein the bioactive glass composition comprises a coating on a biostable material of the implant.

14. An implant according to claim 7, wherein the implant comprises at least one pyrrolidone.

* * * * *